United States Patent [19]

Broger et al.

[11] Patent Number: 5,543,559
[45] Date of Patent: Aug. 6, 1996

[54] PROCESS FOR THE ENANTIOSELECTIVE HYDROGENATION OF KETOSIOPHORONE DERIVATIVES

[75] Inventors: Emil A. Broger, Magden; Yvo Crameri, Oberwil; Rudolf Schmid, Arlesheim; Theodor Siegfried, Riehen, all of Switzerland

[73] Assignee: Hoffman-La Roche Inc., Nutley, N.J.

[21] Appl. No.: 482,210

[22] Filed: Jun. 8, 1995

[30] Foreign Application Priority Data

Jul. 7, 1994 [CH] Switzerland ............... 2173/94

[51] Int. Cl.$^6$ ............... C07C 69/02; C07C 69/76; C07C 69/96; C07C 271/34
[52] U.S. Cl. ............... 560/231; 558/260; 558/276; 560/106; 560/162; 560/259
[58] Field of Search ............... 558/260, 276; 560/106, 162, 231, 259

[56] References Cited

PUBLICATIONS

Takaya et al, Catalytic Asymmetric Synthesis, pp. 1–36 month not available (1993).
Mayer, et al. Helevtica Chimica Acta, vol. 63, pp. 1451–1455, month not available (1980).
Brunner, et al. Journal of Organometallic Chemistry, vo. 456, pp. 71–75 month not available (1993).

*Primary Examiner*—Johann Richter
*Assistant Examiner*—Laura L. Stockton
*Attorney, Agent, or Firm*—George M. Gould; William H. Epstein

[57] ABSTRACT

The present invention is concerned with a process for the manufacture of optically active compounds of the formula

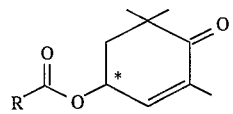

I wherein R signifies lower alkyl, lower alkoxy, phenyl, benzyl or —$NR_2^1$, $R^1$ signifies lower alkyl, phenyl, benzyl or hydrogen and * signifies an optically active center, by asymmetrically hydrogenating an enol derivative of ketoisophorone of the formula

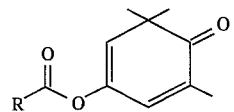

II wherein R has the significance given above, in the presence of a rhodium complex of an optically active diphosphine ligand.

6 Claims, No Drawings

PROCESS FOR THE ENANTIOSELECTIVE HYDROGENATION OF KETOSIOPHORONE DERIVATIVES

BACKGROUND OF THE INVENTION

This invention relates to a process for the enantioselective hydrogenation of derivatives of ketoisophorone, of the formula

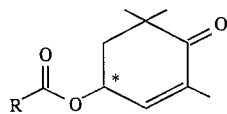

in the presence of a cationic rhodium complex.

It is known that compounds of formula I, which can be converted by hydrolysis into phorenol (1) and in a further reaction step into optically active actinol (2), are important intermediates for the manufacture of 3-hydroxy-carotenoids, especially zeaxanthin (Helv. Chim. Acta 63 (1980), 1451). Diverse attempts have hitherto been made to directly enantioselective hydrogenate ketoisophorone (3) used as the educt for the synthesis of actinol (2). In these, the diketone (6) was obtained as the main product not only with ruthenium but also with rhodium catalysts, the optical yields were, however, only low. Attempts have also been made to produce a more suitable substrate for the hydrogenation by derivatizing ketoisophorone (3). Thus, for example, the asymmetric hydrogenation of the cyclic acetal (5) and subsequent hydrolysis gave the diketone (6) with only 10% enantiomeric excess (ee), while in the asymmetric hydrogenation of the methyl enol ether (4) the diketone (6) was obtained with 50% ee (Brunner et al. J. Organomet. Chem. 456 (1993), 71 and Literature cited therein).

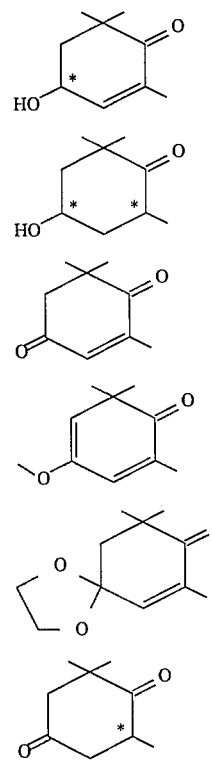

The present invention now provides an industrially access to s actinol (2) by asymmetric hydrogenation. It has been found that the enantioselective hydrogenation of acyl derivatives of ketoisophorone in the presence of a cationic rhodium complex with chiral diphosphine ligands in suitable solvents leads to the corresponding acyl derivatives of phorenol in high optical yields which further can be converted to actinol (2).

BRIEF SUMMARY OF THE INVENTION

The invention is directed to a novel process for the manufacture of compounds of the formula

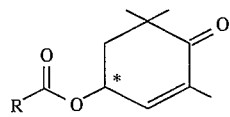

wherein R signifies lower alkyl, lower alkoxy, phenyl, benzyl or —$NR_2^1$, $R^1$ signifies lower alkyl, phenyl, benzyl or hydrogen and * signifies an optically active centre, which process comprises asymmetrically hydrogenating an enol derivative of ketoisophorone of the formula

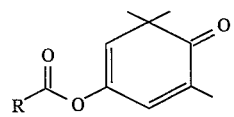

wherein R has the significance given above, in the presence of a catinoic rhodium complex of an optically active diphosphine ligand.

DETAILED DESCRIPTION OF THE INVENTION

The invention is directed to a novel process for the manufacture of compounds of the formula

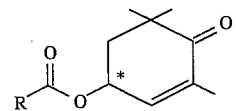

wherein R signifies lower alkyl, lower alkoxy, phenyl, benzyl or —$NR_2^1$, $R^1$ signifies lower alkyl, phenyl, benzyl or hydrogen and * signifies an optically active centre, which process comprises asymmetrically hydrogenating an enol derivative of ketoisophorone of the formula

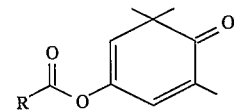

wherein R has the significance given above, in the presence of a cationic: rhodium complex of an optically active diphosphine ligand.

A preferred embodiment of the process in accordance with the invention is concerned with the manufacture of the (R)- or (S)-enantiomer of the compound of the formula

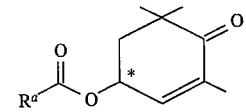

wherein $R^a$ signifies lower alkyl, especially methyl, by the asymmetric hydrogenation of the corresponding compound of the formula

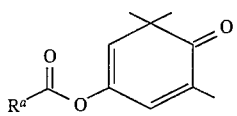

II-a wherein $R^a$ has the significance given above.

Cationic rhodium complexes of the formula III are used as catalysts in accordance with the invention

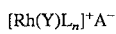   III wherein

L signifies a neutral ligand, n signifies 0, 1 or 2, $A^-$ signifies anion, and

Y signifies a chiral diphosphine.

When Y is a chiral diphosphine any chiral diphosphine group can be used.

Especially suitable are chiral diphosphine groups of the formula

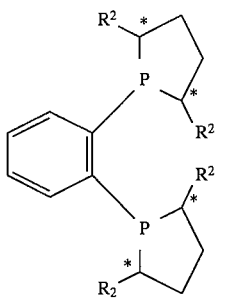   IV

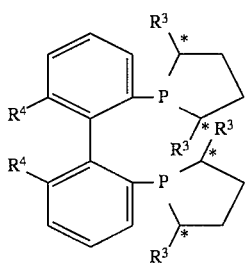   V

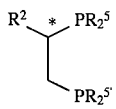   VI

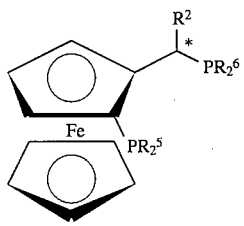   VII

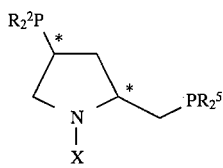   VIII or

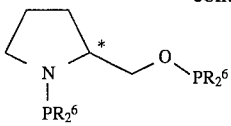   IX wherein

X signifies $-COR^6$, $COOR^6$, $CONR_2^3$, $SO_2R^6$ or $POR_2^5$, $R^2$ signifies cycloalkyl or alkyl, $R^3$ signifies hydrogen, cycloalkyl or alkyl, $R^4$ signifies lower alkyl or lower alkoxy, $R^5$ and $R^{5'}$ each independently signify aryl or heteroaryl and $R^6$ signifies aryl, heteroaryl, cycloalkyl or alkyl.

The term "neutral ligand" signifies in the scope of the present invention any readily exchangeable ligand such as an olefin, e.g. ethylene, propylene, cyclooctene, 1,5-hexadiene, norbornadiene, 1,5-cyclooctadiene and the like or a nitrile such as acetonitrile or benzonitrile. The ligand can also be exchanged during the hydrogenation. Where more than one such ligand is present, these can also be different from one another.

When $A^-$ is a anion any anion can be used. Examples of such anions include $BF_4^-$, $CF_3SO_3^-$, $PF_6^-$, $ClO_4^-$ or $B(C_6H_5)_4^-$.

The term "lower alkyl" as used for formulas I, II and V signifies in the scope of the present invention straight-chain or branched alkyl groups with 1 to 4 carbon atoms such as methyl, ethyl, propyl, isopropyl, n-butyl, isobutyl and tert-.butyl. The term "lower alkoxy" as used in formulas I, II and V signifies groups in which the alkyl residue has the foregoing significance.

In the scope of the present invention both the phenyl and benzyl groups referred to in connection with the compounds of formulas I and II can be substituted or unsubstituted when substituted the preferred substitution groups are lower alkyl or lower alkoxy in the ortho-, meta- or para- position.

The term alkyl as used for $R^2$, $R^3$ and R6 signifies straight-chain or branched alkyl groups with 1 to 7 carbon atoms. Cycloalkyl signifies in this connection cyclopropyl, cyclobutyl, cyclopentyl, cyclohexyl or cycloheptyl.

The term "aryl" as used in connection with the compounds of formulas VI, VII, VIII and IX signifies a substituted or unsubstituted aromatic hydrocarbon. Any aryl group can be used. The preferred aryl is phenyl which optionally can be substituted in the ortho-, meta- or para-position by lower alkyl or lower alkoxy, preferably methyl or methoxy, or di-lower alkylamino, preferably dimethylamino, where lower alkyl and lower alkoxy is as defined above.

The term "heteroaryl" signifies an aryl group where at least one carbon atom in the aromatic ring structure is a hetero atom such as S, O, N. Preferably the heteroaryl residue is a residue of the formula

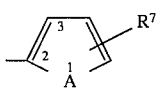   (a)

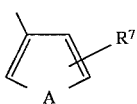   (b)

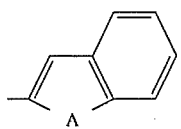

or

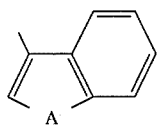

In the residues of formulas (a) to (d), A signifies, in turn, oxygen, sulphur or —NR$^8$. The substituent R$^7$ signifies hydrogen, lower alkyl, especially methyl, or lower alkoxy, especially methoxy, and R$^8$ stands for lower alkyl, preferably methyl, whereas lower alkyl and lower alkoxy are as defined above.

Cationic rhodium complexes of formula III with the chiral diphosphine ligands of formulas IV–IX, especially with diphosphine ligands of formulas IV, VI and VII, are suitable for the process in s accordance with the invention. Very high selectivities are achieved in the process in accordance with the invention when cationic rhodium complexes of formula III with chiral diphosphine ligands of formulas IV and VII are used. An especially high selectivity with an almost quantitative conversion of the substrate II and high optical o yields can be attained especially using rhodium complexes with chiral diphosphine ligands of formula IV in which R$^2$ signifies methyl or ethyl.

The cationic rhodium complexes of formula III can be prepared by methods known in the art. The rhodium complexes of formula III can be prepared in a manner known per se, e.g. according to the process described in EP-A-0 574 783 by reacting a compound of formulas IV to IX with a rhodium-yielding compound in a suitable, inert solvent.

The chiral diphosphines of formulas IV and V are known compounds and can be prepared, for example, as described in U.S. Pat. No. 5,171,892. The chiral diphosphines of formula VI are also known compounds and can be prepared, for example, according to the process described in EP-A-031 877. The chiral diphosphines of formula VII can be obtained analogously to EP-A-564 406, while a practicable process for the preparation of the diphosphines of formula VIII is described in EP-A-251 164. A preparation method for the diphosphines of formula IX is described in Tetrahedron: Asymmetry 1993, Vol. 4, 2279.

Next is described the enantioselective hydrogenation of compounds of formula II. This process can be carried out in an aprotic medium which is inert towards this compound, such as an ester, ether or a hydrocarbon. Esters such as ethyl acetate, cyclic ethers such as, for example, tetrahydrofuran or dioxan, aromatic hydrocarbons such as benzene or toluene or also mixtures thereof are especially suitable solvents which can be used.

The ratio between rhodium and the ligand Y in the complex of formula III conveniently lies between about 0.05 and 5 mol, preferably between 0.5 and 2 mol, of rhodium per mol of ligand. The molar ratio between rhodium in the complex of formula III and the compound of formula II to be hydrogenated conveniently lies between about 0.001 and about 5 mol %, preferably between about 0.002 and about 0.2 mol %; i.e. the substrate/catalyst ratio (S/C) is 100,000 to about 20, especially about 50,000 to about 500. The enantioselective hydrogenation of compounds of formula II using a complex of formula In can be effected at temperatures of about 0° C. to about 120° C., preferably at about 10° C. to about 60° C., however the temperature is not critical. The hydrogenation is effected under pressure, conveniently under a pressure of about 1 to 150 bar, preferably of 5 to 60 bar, however the pressure is not critical. The compounds of formula II are known compounds and can be prepared by methods known in the art.

The following Examples illustrate the invention and are in no way a limitation.

GC=capillary gas chromatography
o.p.=optical purity
ee=enantiomeric excess
(R,R)-Et-DuPHOS=1,2-bis[(2R,5R)-2,5-diethylphospholano]-benzene
(S,S)-Et-DuPHOS=1,2-bis[(2S,5S)-2,5-diethylphospholano]-benzene
(R,R)-Me-DuPHOS=1,2-bis[(2R,5R)-2,5-dimethylphospholano]-benzene
(S,S)-Me-DuPHOS=1,2-bis[(2S,5S)-2,5-dimethylphospholano]-benzene
(R)-PROPHOS=(R)-1,2-bis(diphenylphosphino)propane
(S,S)-BCPM=(2S,4S)-1-tert-butoxycarbonyl-4-dicyclohexylphosphino-2-diphenylphosphino-methylpyrrolidine
(R,S)-PPF-PCy$_2$={(R)-1-[(S)-2-(diphenylphosphino)ferrocenyl}ethyl-dicyclohexylphosphine
(R,S)-PPF-P(o-An)$_2$={(R)-1-[(S)-2-(diphenylphosphino)ferrocenyl]}-ethyl-di-(o-methoxyphenyl)phosphine
(S,S,S)-MePHOS-MeOBIPHEP=(2S,5S)-1-{(S)-2'-[(2S,5S)-2,5-dimethyl-phospholan-1-yl]-6,6'-dimethoxybiphenyl-2-yl}-2,5-dimethyl-phospholane
(S)-MeOBIPHEPHOS=1-{(S)-2'-(phospholan-1-yl)-6,6'-dimethoxybiphenyl-2-yl}-phospholane
(S,S,S)-MePHOS-MeOBIPHEP=(2S,5S)-1-{(S)-2'-[(2S,5S)-2,5-dimethyl-phospholan-1-yl]-6,6'-dimethoxybiphenyl-2-yl}-2,5-dimethyl-phospholane
(S,S,R)-MePHOS-MeOBIPHEP=(2S,5S)-1-{(R)-2'-[(2S,5S)-2,5-dimethyl-phospholan-1-yl]-6,6'-dimethoxybiphenyl-2-yl}-2,5-dimethyl-phospholane
Cy$_4$-5-OxoProNOP=(R)-1-dicyclohexylphosphanyl-5-(dicyclohexyl-phosphanoyloxymethyl)pyrrolidine-2-one.

EXAMPLE 1

10.5 mg (0.026 mmol) of bis-(1,5-cyclooctadiene)rhodium(I) tetrafluoroborate and 9.4 mg (0.026 mmol) (R,R)-Et-DuPHOS were placed in a 20 ml measuring flask in a glove box (O$_2$ content<1 ppm) and made up to mark with about 20 ml of ethyl acetate. The orange catalyst solution obtained was stirred at 22° for 10 min.

Then, 25.0 g (128.7 mmol) of 4-acetoxy-2,6,6-trimethylcyclohexa-2,4-dien-1-one (prepared according to Helv. Chim. Acta 1989, 72,365 and additionally crystallized from n-hexane, m.p. 44°–45° C.) and 20 ml of ethyl acetate were placed in a 185 ml steel autoclave in the glove box. 10 ml of the above-prepared catalyst solution (S/C 10,000) were added to this suspension and the autoclave was sealed. The hydrogenation was carried out at 20° C., a constant pressure of 10 bar and while stirring intensively.

The conversion was 100% after 21 hours. The hydrogenation solution consisted of a mixture of 92.8% GC-area percent 4-acetoxy-2,6,6-trimethyl-2-cyclohexen-1-one and 7.2% 4-acetoxy-2,6,6-trimethyl-4-cyclohexen-1-one.

For the ee determination, a sample of the hydrogenation solution containing about 20 mg of product was evaporated at 50° C./17 mbar, the residue was dissolved in 1 ml of methanol and converted by heating to 50° C. for 30 min.

with 20 mg of sodium methylate into a mixture of 92% (4S)-4-hydroxy-2,6,6-trimethyl-2-cyclohexen-1-one (98.5% ee) and 8% 2,2,6-trimethyl-cyclohexane-1,4-dione. The ee determination was effected after acidifying with about 60 ml of acetic acid by gas chromatography on a chiral phase (permethylated β-cyclodextrin mixed with OV-61).

For the working-up, the hydrogenation solution, flushed from the autoclave, was evaporated at 45° C./20 mbar. The residue, 25.2 g of dark yellow oil, was dissolved in 125 ml of methanol and 25 ml of water and added dropwise at 20° C. to 25.5 ml of 5N aqueous sodium hydroxide solution. After stirring at 20° C. for one hour the methanol was evaporated at 50° C./23 mbar. The aqueous phase was extracted with diethyl ether. After drying and evaporating the organic phase there were obtained 18.9 g of orange oil which was chromatographed on 500 g of silica gel with n-hexane/ether 3/1. There were obtained 17.8 g (90%) of (4S)-4- hydroxy- 2,6,6-trimethyl-2-cyclohexen-1-one as a pale yellow oil; chem. purity 99.2 GC-area%; 98.5% ee; $[\alpha]_D = -48.8°$ (c=1, EtOH).

EXAMPLE 2 a) Synthesis of 4-tert.-butyloxycarbonyloxy-2,6,6-trimethylcyclohexa-2,4-dienone:

A solution of 23.2 g (106.3 mmol) of di-tert.-butyl dicarbonate in 25 ml of tetrahydrofuran was added dropwise to a suspension, stirred at 24° C., of 20.0 g (144.7 mmol) of $K_2CO_3$, 20 ml of tetrahydrofuran, 1.1 g (4.2 mmol) of 18-crown-6 and 15.2 g (100 mmol) of ketoisophorone. The suspension was stirred at 60° C. for 5 hours, then the brown reaction mixture was filtered and finally the solvent was evaporated. The brown residue (26.6 g) was dissolved in 200 ml of dichloromethane and the solution was extracted with saturated NaHCO3 solution and with water. The organic phase was dried over $Na_2SO_4$, filtered and evaporated. The brown residue (22.6 g) was chromatographed over 150 g of silica gel (n-hexane/ether 2/1). There were obtained 20.4 g (81%) of 4-tert.-butyloxycarbonyloxy-2,6,6-trimethylcyclohexa-2,4-dienone as a yellow oil; anal. calc. for $C_{14}H_{20}O_4$ (252.31): C 66.65, H 7.99; found: C 66.46, H 8.08. $^1$H-NMR (250 MHz, CDCl$_3$): 1.25 (s, 2 CH$_3$—C(6)); 1.54 (s, (CH$_3$)$_3$C—O); 1.91 (s, CH$_3$—C(2); 5.88–5.89 (d, H—C(5)); 6.71–6.74 (m, H—C(5)

b) Hydrogenation of 4-tert.-butyloxycarbonyloxy-2,6,6-trimethylcyclohexa-2,4-dienone:

40.3 mg (0.099 mmol) bis-(1,5-cyclooctadiene)rhodium(I) tetrafluoroborate and 35.9 mg (0.099 mmol) (R,R)-Et-DuPHOS were placed in a 20 ml measuring flask in a glove box (O$_2$ content <1 ppm) and made up to mark with about 20 ml of ethyl acetate. The orange catalyst solution obtained was stirred at 22° C. for 10 min.

2.5 g (9.9 mmol) of 4-tert.-butyloxycarbonyloxy-2,6,6-trimethylcyclohexa-2,4-dienone and 47 ml of ethyl acetate were placed in a 185 ml steel autoclave in the glove box, 20 ml of the above-prepared catalyst solution (S/C 100) were added and the autoclave was sealed. The hydrogenation was carried out at 20° C., a constant pressure of 10 bar and while stirring intensively.

The conversion was 100% after 5 hours. The hydrogenation solution consisted of a mixture of 98 GC-area% 4-tert.-butyloxycarbonyloxy-2,6,6-trimethyl-2-cyclohexen-1-one and 2% 4-tert.-butyloxycarbonyloxy-2,6,6-trimethyl-4-cyclohexen-1-one.

For the ee determination, a sample of the hydrogenation solution containing about 20 mg of product was evaporated at 50° C./17 mbar, the residue was dissolved in 1 ml of methanol and converted by heating to 50° C. for 30 min. with 20 mg of sodium methylate into a mixture of 98% (4S)-4-hydroxy-2,6,6-trimethyl-2-cyclohexen-1-one (87.3% eel and 2% 2,2,6-trimethyl-cyclohexane-1,4-dione. The ee determination was effected after acidifying with about 60 ml of acetic acid by gas chromatography on a chiral phase (permethylated β-cyclodextrin mixed with OV-61 ).

EXAMPLE 3 a) Synthesis of 4-benzyloxy 2,6,6-trimethylcyclohexa-2,4-dien-1-one:

A mixture of 91.3 g (0.6 mol) of ketoisophorone, 600 g (2.65 mol) of benzoic anhydride, 251 mL (1.8 mol) of triethylamine and 3.66 g (0.03 mol) of 4-(dimethylamino)pyridine was stirred at 65° C. under argon for 18 hours and diluted with 1 l of ether. 260 ml of ethylenediamine were added dropwise at 0°–10° while cooling. The precipitate was filtered off and washed with 1.5 l of ether. The combined filtrate was extracted with saturated NaHCO$_3$ solution (1 l), then with saturated sodium chloride solution, dried over Na$_2$SO$_4$ and evaporated. The crude product (137.8 g), a brown crystalline residue, was chromatographed over silica gel (n-hexane/ether 5/1). 117.4 g (76.3%) of 4-benzoyloxy 2,6,6-trimethylcyclohexa-2,4-dien-1-one were obtained as a yellow crystallizate. Recrystallization from tert.-butyl methyl ether/n-hexane (1/1) yielded pure benzoate, m.p. 64°–66° C.

b) Hydrogenation of 4-benzoyloxy 2,6,6-trimethylcyclohexa-2,4-alien-i-one:

19.8 mg (0.049 mmol) of bis-( 1,5-cyclooctadiene)rhodium(I)-tetrafluoroborate and 17.7 mg (0.049 mmol) of (S,S)-Et-DuPHOS were placed in a 20 ml measuring flask in a glove box (02 content<1 ppm) and made up to mark with about 20 ml of ethyl acetate. The orange catalyst solution obtained was stirred at 22° for 10 min.

Then, 2.5 g (9.75 mmol) of 4-benzoyloxy-2,6,6-trimethylcyclohexa-2,4-dien-1-one and 62.6 ml of ethyl acetate were placed in a 185 ml steel autoclave in the glove box, 4 ml of the aboveprepared catalyst solution (S/C 1000) were added and the autoclave was sealed. The hydrogenation was carried out at 20° C., a constant pressure of 10 bar and while stirring intensively.

The conversion was 100% after 43 hours. The hydrogenation solution consisted of a mixture of 96% GC-area% 4-benzoyloxy-2,6,6-trimethyl-2-cyclohexen-1-one and 4% 4-benzoyloxy-2,6,6-trimethyl-4-cyclohexen-1-one. For the ee determination, a sample of the hydrogenation solution containing about 20 mg of product was evaporated at 50° C./17 mbar the residue was dissolved in 1 ml of methanol and converted by heating to 50° C. for 30 min. with 20 mg of sodium methylate into a mixture of 96% (4R)-4-hydroxy-2,6,6-trimethyl-2-cyclohexen-1-one (91.2% ee) and 4% 2,2,6-trimethylcyclohexane-1,4-dione. The ee determination was effected after acidifying with about 60 ml of acetic acid by gas chromatography on a chiral phase (permethylated β-cyclodextrin mixed with OV-61 ).

EXAMPLES 4–21: see Table 1.

TABLE 1

Asymmetric hydrogenation of acetate in presence of [Rh(P̂ P)]X[5)]

| No. | P̂ P | X | S/C | Solvents | c % | p bar | T °C. | % Conversion after 20 h | Select. %[1)] | ee (S) % |
|---|---|---|---|---|---|---|---|---|---|---|
| 4 | (R,R)-Et—DuPHOS | CF$_3$SO$_3$ | 100 | Ethyl acetate | 4 | 10 | 20 | 100 | 77 | 92.7 |
| 4a | (R,R)-Me—DuPHOS | BF$_4$ | 15000 | Methyl acetate | 48 | 10 | 20 | 100 | 93 | 97.5 |
| 5 | (R,R)-Et—DuPHOS | PF$_6$ | 100 | Ethyl acetate | 4 | 10 | 20 | 100 | 84 | 92.0 |
| 6 | (R,R)-Me—DuPHOS | BF$_4$ | 10000 | Ethyl acetate | 48 | 10 | 20 | 100 | 95 | 98.5 |
| 7 | (R,R)-Et—DuPHOS | CF$_3$SO$_3$ | 200 | Ethyl acetate | 4 | 5 | 20 | 99 | 78 | 90.7 |
| 8 | (R,R)-Et—DuPHOS | BF$_4$ | 10000 | Ethyl acetate | 80 | 10 | 20 | 100 | 91 | 98.3 |
| 9 | (R,R)-Et—DuPHOS | BF$_4$ | 10000 | Ethyl acetate | 24 | 50 | 20 | 99 | 92 | 96.4 |
| 10 | (R,R)-Et—DuPHOS | BF$_4$ | 10000 | Ethyl acetate | 24 | 10 | 60 | 96 | 89 | 96.9 |
| 11 | (R,R)-Et—DuPHOS | BF$_4$ | 10000 | Ethyl acetate | 24 | 50 | 60 | 94 | 91 | 97.1 |
| 12 | (R,R)-Et—DuPHOS | BF$_4$ | 10000 | Ethyl acetate | 12 | 10 | 100 | 99 | 85 | 89.2 |
| 13 | (R,R)-Et—DuPHOS | BF$_4$ | 500 | Tetrahydrofuran | 12 | 10 | 20 | 100 | 83 | 97.5 |
| 14 | (R,R)-Et—DuPHOS | BF$_4$ | 500 | Toluene | 12 | 10 | 60 | 99 | 80 | 83.8 |
| 15 | (R,S)-PPF—PCy$_2$ | BF$_4$ | 100 | Ethyl acetate | 8 | 10 | 20 | 100 | 22[2)] | 79.6 |
| 16 | (R,S)-PPF—P(tBu)$_2$ | BF$_4$ | 100 | Ethyl acetate | 8 | 10 | 20 | 100 | 12[3)] | 94.2 |
| 16a | (R,S)-PPF—P(tBu)$_2$ | BF$_4$ | 5000 | Ethyl acetate | 12 | 10 | 20 | 78 | 97 | 83.9 |
| 16b | (R,S)-PPF—P(o-An)$_2$ | BF$_4$ | 1000 | Ethyl acetate | 12 | 10 | 20 | 97 | 61 | 86.3 |
| 17 | (S,S)-BCPM | BF$_4$ | 100 | Ethyl acetate | 8 | 10 | 20 | 100 | 47[4)] | 89.8(R) |
| 18 | (R)-PROPHOS | CF$_3$SO$_3$ | 100 | Ethyl acetate | 4 | 10 | 20 | 100 | 65 | 81.3 |
| 19 | (S,S,S)-MePHOS—McOBIPHEP | BF$_4$ | 100 | Ethyl acetate | 12 | 10 | 20 | 96 | 70 | 70.8 |
| 20 | (S,S,R)-MePHOS—McOBIPHEP | BF$_4$ | 100 | Ethyl acetate | 12 | 10 | 20 | 100 | 47 | 60.9 |
| 21 | (S)-McOBIPHEPHOS | BF$_4$ | 100 | Ethyl acetate | 8 | 10 | 20 | 100 | 48 | 58.7 |
| 22 | (S)-Cy$_4$-oxoProNOP | BF$_4$ | 1000 | Ethyl acetate | 12 | 10 | 20 | 100[6)] | 79 | 90.6(R) |

[1)] Byproduct: 4-Acetoxy-2,6,6-trimethyl-4-cyclohexen-1-one
[2)] Byproduct: 64 GC-area % 4-acetoxy-2,6,6-trimethyl-4-cyclohexan-1-one
[3)] Byproduct: 77 GC-area % 4-acetoxy-2,6,6-trimethyl-4-cyclohexan-1-one
[4)] Byproduct: 65 GC-area % 4-acetoxy-2,6,6-trimethyl-4-cyclohexan-1-one

[5)] Catalyst prepared in situ starting from [Rh(COD)$_2$]X + P̂ P as in ex. 1
[6)] Conversion after 6 hours

We claim:

1. A process for the manufacture of optically active compounds of the formula

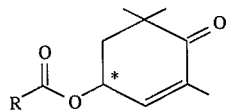

I wherein R signifies lower alkyl, lower alkoxy, phenyl, benzyl or —NR$_2^1$, R$^1$ signifies lower alkyl, phenyl, benzyl or hydrogen and * signifies an optically active centre, which process comprises asymmetrically hydrogenating an enol derivative of ketoisophorone of the formula

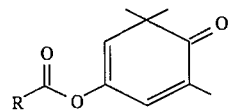

II wherein R has the significance given above, in the presence of a cationic rhodium complex of an optically active diphosphine ligand.

2. A process according to claim 1, wherein the cationic rhodium complexes is of the formula

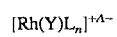

III wherein

L signifies a neutral ligand, n signifies 0, 1 or 2,

A$^-$ signifies an anion, and

Y signifies a chiral diphosphine.

3. A process according to claim 2, wherein the chiral diphosphine is a compound of the formula

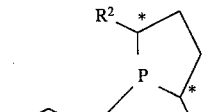

IV

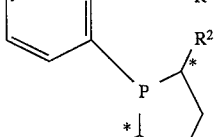

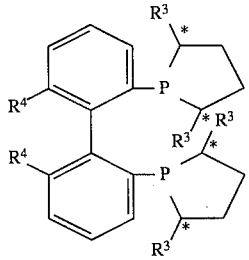

V

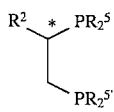

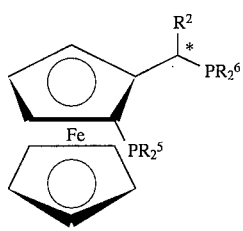

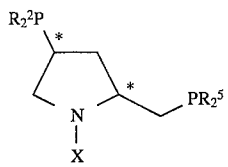

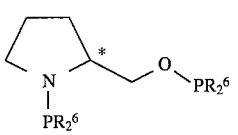

wherein

X signifies —COR$^6$, COOR$^6$, CONR$_2^3$, SO$_2$R$^6$ or POR$_2^5$,

R$^2$ signifies cycloalkyl or alkyl,

R$^3$ signifies hydrogen, cycloalkyl or alkyl,

R$^4$ signifies lower alkyl or lower alkoxy,

R$^5$ and R$^{5'}$ each independently signify aryl or heteroaryl and

R$^6$ signifies aryl, heteroaryl, cycloalkyl or alkyl.

4. A process according to claim 2 wherein the anion is selected from the group consisting of BF$_4^-$, CF$_3$SO$_3^-$, PF$_6^-$, CLO$_4^-$ and B(C$_6$H$_5$)$_4^-$.

5. A process according to claim 3, wherein the chiral diphosphine is a compound of formulas IV or VII.

6. A process according to claim 3, wherein the chiral diphosphine is a compound of formula IV in which R$^2$ signifies methyl or ethyl.

* * * * *

UNITED STATES PATENT AND TRADEMARK OFFICE
CERTIFICATE OF CORRECTION

PATENT NO. : 5,543,559
DATED : August 6, 1996
INVENTOR(S) : Emil A. Broger, Rudolf Schmid and Theodor Siegfried It is certified that error appears in the above-indentified patent and that said Letters Patent is hereby corrected as shown below:

Line 5,
In the Absract, change "$NR_2^1$" to -- $NR_2^1$ --.

Column 2, line 17, change "$NR_2^1$" to -- $NR_2^1$ --.

Column 2, line 43, change "$NR_2^1$" to -- $NR_2^1$ --.

Column 9, line 51, change "$NR_2^1$" to -- $NR_2^1$ --.

Signed and Sealed this

Eighth Day of April, 1997

*Attest:*

BRUCE LEHMAN

*Attesting Officer*     Commissioner of Patents and Trademarks